Sept. 10, 1968 D. L. ARMSTRONG ET AL Plant Pat. 2,832
ROSE PLANT
Filed Feb. 27, 1967
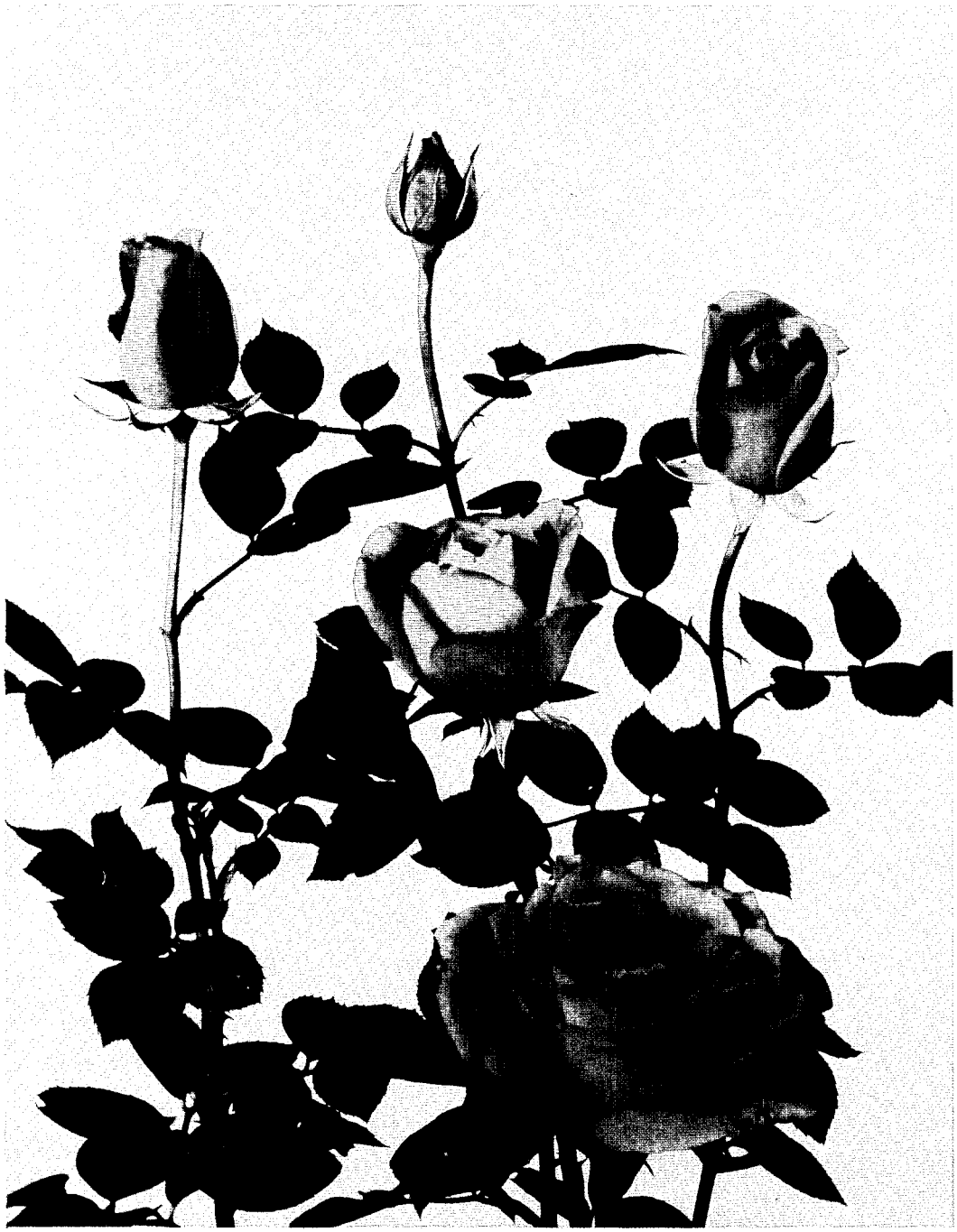
Inventors.
D. L. Armstrong
H. C. Swim
By: Robb & Robb
Attorneys.

United States Patent Office

Plant Pat. 2,832
Patented Sept. 10, 1968

2,832
ROSE PLANT

David L. Armstrong and Herbert C. Swim, Ontario, Calif., assignors to Armstrong Nurseries, Inc., Ontario, Calif., a corporation of California Filed Feb. 27, 1967, Ser. No. 619,077
1 Claim. (Cl. Plt.—20)

The present invention relates to a new and distinct variety of rose plant of the hybrid tea class, which was originated by us by crossing an unnamed and unpatented seedling of unidentified parentage with the variety known as "Chrysler Imperial" (Plant Patent No. 1,167), the former being the seed parent, and the latter being the pollen parent. The unnamed seed parent was a very vigorous, upright, relatively thornless, semi-double light red flowered hybrid tea rose variety which bore flowers on exceptionally long stems and whose flowers had a moderately strong fragrance.

The new variety resulted from an extensive breeding program having for its primary objective to produce improved red flowered hybrid tea rose varieties particularly emphasizing flower fragrance, bud and flower form, rich red flower color, and good plant habit with adequate vigor of growth. This objective was fully achieved, along with other desirable features, as evidenced by the following unique combination of characteristics which are outstanding in the new variety and which distinguish it from its parents, as well as from all other varieties of which we are aware:

(1) A moderately vigorous, attractive and upright plant habit;

(2) Medium sized, dark green leathery and semi-glossy mature foliage, contrasting with attractive dark reddish new growth;

(3) Relatively few thorns;

(4) A floriferous habit, with the flowers generally borne singly on medium length to long stems;

(5) Attractive urn-shaped buds which develop into high-centered half-open and open flowers of good form;

(6) Medium to large sized flowers having good petalage;

(7) A distinctive and attractive flower color ranging between Rose Red and Cardinal Red; and (8) A rich, strong and spicy flower fragrance.

In comparison with its unnamed seed parent, the new variety primarily differs therefrom by its more double and darker red flowers, with better urn-shaped buds and open flower form, together with a stronger fragrance than the flowers of this parent, but having a somewhat less vigorous plant habit, though adequate, with medium to long stems instead of the exceptionally long stems of this parent.

As compared with its pollen parent "Chrysler Imperial," the new variety primarily differs therefrom by having a more upright plant habit, with somewhat longer single stems, together with a slightly more open habit or less dense foliage, and the flowers of the new variety have fewer petals on an average than those of this parent.

Asexual reproduction of our new variety by budding, as performed at Ontario, Calif., shows that the foregoing characteristics and distinctions come true to form and are established and transmitted through succeeding propagations.

The accompanying drawing shows typical specimens of the vegative growth and flowers of our new variety in different stages of development as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as (W)) and Robert Ridgway's Color Standards and Nomenclature (hereinafter abbreviated as (R)), as indicated:

Type: Bush; outdoors; seedling; for cut flowers and for garden decoration.

Class: Hybrid tea.

Breeding: Seedling.

*Seed parent.*—An unnamed seedling of unidentified parentage.

*Pollen parent.*—"Chrysler Imperial."

Propagation: Holds its distinguishing characteristics through succeeding propagations by budding.

*Flower*

Locality where grown and observed: Ontario, Calif.

Flowers borne: Usually singly, but sometimes two or three to stem; in irregular clusters; on medium to long stems of normal strength.

Quantity of bloom: Free, outdoors.

Continuity: Nearly continuous during growing season.

Fragrance: Strong. Nature—spicy.

Bud:

*Peduncle.*—From average length to long; average caliper; erect; usually smooth; with few to several small stipitate glands and none to few hairs. Color—near Buffy Brown, Plate XL (R), overlaid with near Prussian Red, Plate XXVII (R) on side exposed to the sun.

*Before calyx breaks.*—Size—medium. Form—from short to medium length; ovoid.

*As calyx breaks.*—Color—between Indian Lake, Plate 826, page 170 (W) and Purple Madder, Plate 1028, page 181 (W).

*Sepals.*—Usually with foliaceous appendages extending from ¼ to ½ of sepal length. Inner surface—with fine, wooly tomentum. Outer surface—usually smooth. Alternate margins—lined with fine, wooly tomentum. Other margins—with none to few small stipitate glands and small, slender foliaceous parts.

*As first petal opens.*—Size—average. Form—medium length; ovoid; urn-shaped. Color: outside—between Cardinal Red, Plate 822/2, page 168 (W) and Chrysanthemum Crimson, Plate 824/3, page 169 (W); inside—near Cardinal Red, Plate 822/1, page 168 (W), with small area at base of petal near attachment near Lemon Yellow, Plate 4/1, page 4 (W).

*Opening.*—Opens up well; is not retarded or prevented from opening by cold, hot, wet or dry weather.

Bloom:

*Size (when fully open).*—From average to large; from 3½ inches to 5 inches.

*Petalage.*—Double; from 25 to 35 petals, plus 8 to 10 petaloids; arranged irregularly.

*Form.*—High-centered at first, but becoming cupped to high-centered; petals being at first tightly cupped, but later becoming more loosely flat to cupped, with tips reflexed outwardly at maturity; outside petals of newly opened flowers usually reflexed outward along the apex; outside and intermediate petals of three days open flowers usually reflexed outward both along apex and edges.

Petals:

*Texture.*—Medium thickness; from moderately leathery to soft.

*Appearance.*—Inside—slightly satiny. Outside—satiny.

*Shape.*—Outside—between round and broadly obovate, with apex flat and sometimes with 1 or 2 notches. Intermediate—broadly obovate, with apex rounded to flat and sometimes with 1 or 2 notches. Inside—obovate, with apex rounded.

This description of a newly opened flower was made from a rose grown outdoors during the month of November at Ontario, Calif.:

*Color.*—Outer petal: outside surface—between Cardinal Red, Plate 822/1, page 168 (W) and Chrysanthemum Crimson, Plate 824/3, page 169 (W); inside surface—near Cardinal Red, Plate 822/1, page 168 (W) with small area at base of petal near attachment near Lemon Yellow, Plate 4/1, page 4 (W). Intermediate petal: outside surface—between Cherry, Plate 722/2, page 157 (W) and Rose Red, Plate 724/1, page 158 (W); inside surface—between Rose Red, Plate 724, page 158 (W) and Cardinal Red, Plate 822/2, page 168 (W), with small area at base of petal near attachment near Lemon Yellow, Plate 4/2, page 4 (W). Inner petal: outside surface—between Cherry, Plate 722, page 157 (W) and Rose Red, Plate 724, page 158 (W); inside surface—between Rose Red, Plate 724, page 158 (W) and Cardinal Red, Plate 822, page 168 (W), with small area at base of petal near attachment near Lemon Yellow, Plate 4/1, page 4 (W).

This description was made from a rose that was open for three days outdoors during the month of November at Ontario, Calif.:

*Color.*—Outer petal: outside surface—near Rose Red, Plate 724/1, page 158 (W). inside surface—between Rose Red, Plate 724, page 158 (W) and Chrysanthemum Crimsom, Plate 824/3, page 169 (W). Inner petal: outside surface—near Rose Red, Plate 724/1, page 158 (W); inside surface—between Rose Red, Plate 724, page 158 (W) and Chrysanthemum Crimson, Plate 824/3, page 169 (W).

*General color effect.*—Newly opened flower—between Rose Red, Plate 724, page 158 (W) and Cardinal Red, Plate 822/2, page 168 (W). 3-days open—between Rose Red, Plate 724, page 158 (W) and Chrysanthemum Crimson, Plate 824/3, page 169 (W).

*Behavior.*—Drop off cleanly; not particularly affected by cold, hot, wet or dry weather.

*Flower longevity.*—On bush in garden—3 to 5 days in November. Cut roses grown outdoors and kept at living room temperatures—3 or 4 days in November.

*Reproductive organs*

Stamens: From few to average number; arranged regularly about pistils; a few mixed with petaloids.

Filaments: Medium length (from 5 mm. to 12 mm. long); most with anthers. Color—near Cadmium Orange, Plate 8/2, page 8 (W).

Anthers: From small to medium size; all open approximately at once. Color: upper side—margins near Buttercup Yellow, Plate 5/2, page 5 (W), with remainder near Aureolin, Plate 3/3, page 3 (W); under side—margins near Buttercup Yellow, Plate 5/2, page 5 (W), with remainder near Aureolin, Plate 3/3, page 3 (W).

Pollen: From sparse to moderate abundance. Color—near Yellow Ochre, Plate 07/1, page 101 (W).

Pistils: From average number to many (approximately 75).

Styles: Uneven; from short to average length; thin; bunched. Color—upper ½ of style near Cardinal Red, Plate 822/3, page 168 (W), with remainder near Primrose Yellow, Plate 601/3, page 65 (W).

Stigma: Color—near Yellow Ochre, Plate 07/3, page 101 (W).

Ovaries: Usually all enclosed in calyx.

Hips: From short to average length; globular; smooth, walls thick and fleshy. Color (half mature)—near Light Yellowish Olive, Plate XXX (R).

Sepals: Falling soon; medium length; straight. Color: inside—near Vetiver Green, Plate XLVII (R); outside—near Dull Citrine, Plate XVI (R).

Seeds: From few to average number (from 8 to 15); from small to medium size.

*Plant*

Foliage:

*Leaves.*—Compound of usually 3 to 7 leaflets; moderately abundant; medium size; leathery; semi-glossy.

*Leaflets.*—Shape—broadly oval, with apex acute. Base—round. Margin—simply serrate.

*Color.*—Mature: upper surface—near Cress Green, Plate XXXI (R); under surface—near Light Grape Green, Plate XLI (R). Young: upper surface—near Light Cress Green, Plate XXXI (R); under surface—near Grape Green, Plate XLI (R).

*Rachis (the supporting stem of the compound leaf).*—From light to average size. Upper side—grooved; with many small stipitate glands on edges. Under side—smooth; with few to several stipitate glands and none to few small prickles.

*Stipules.*—From short to medium length; narrow; with short points.

*Disease resistance.*—Mildly subject to mildew as compared with other varieties grown under comparable conditions at Ontario, Calif.

Growth:

*Habit.*—Upright; much-branched.

*Growth.*—Moderately vigorous.

*Canes.*—Medium caliper.

*Main stems.*—Color—between Army Brown, Plate XL (R) and Buffy Brown, Plate XL (R). Large prickles—from several to many; short; hooked slightly downward; with narrow base of medium length; color—near Mikado Brown, Plate XXIX (R). Small prickles—few; color—near Mikado Brown, Plate XXIX (R). Hairs—none.

*Branches.*—Color—near Dull Citrine, Plate XVI (R). Large prickles—from few to several; short; hooked slightly downward; with short, narrow base; color—near Sayal Brown, Plate XXIX (R). Small prickles—few; color—near Sayal Brown, Plate XXIX (R). Hairs—none.

*New shoots.*—Color—near Buffy Brown, Plate XL (R), overlaid with near Indian Red, Plate XXVII (R) on side exposed to the sun. Large prickles—from few to several; short; hooked slightly downward; with short, narrow base; color—near Mineral Red, Plate XXVII (R). Small prickles—few; color—near Mineral Red, Plate XXVII (R). Hairs—none.

We claim:

1. A new and distinct variety of rose plant of the hybrid tea class, substantially as herein shown and described, characterized particularly as to novelty by the unique combination of a moderately vigorous, attractive and upright plant habit, medium sized, dark green leathery and semi-glossy mature foliage, contrasting with attractive dark reddish new growth, relatively few thorns, a floriferous habit, with the flowers generally borne singly on medium length to long stems, attractive urn-shaped buds which develop into high-centered half-open flowers of good form, medium to large sized flowers having good petalage, a distinctive and attractive flower color ranging between Rose Red and Cardinal Red; and a rich, strong and spicy flower fragrance.

No references cited.

ROBERT E. BAGWILL, *Primary Examiner.*